(12) United States Patent
Chiu et al.

(10) Patent No.: US 11,045,660 B2
(45) Date of Patent: Jun. 29, 2021

(54) FAR INFRARED FILM STRUCTURE AND METHOD OF MANUFACTURING THE SAME

(71) Applicant: WINE-FONT INTERNATIONAL COMMERCE CORP., New Taipei (TW)

(72) Inventors: Shu-Ching Chiu, New Taipei (TW); Yu-Cheng Li, New Taipei (TW); Yu-Hung Lee, New Taipei (TW)

(73) Assignee: WINE-FONT INTERNATIONAL COMMERCE CORP., New Taipei (TW)

( * ) Notice: Subject to any disclaimer, the term of this patent is extended or adjusted under 35 U.S.C. 154(b) by 661 days.

(21) Appl. No.: 15/883,086

(22) Filed: Jan. 29, 2018

(65) Prior Publication Data

US 2019/0232076 A1   Aug. 1, 2019

(51) Int. Cl.
*A61N 5/06*   (2006.01)
*B32B 15/04*   (2006.01)
*A61F 7/00*   (2006.01)

(52) U.S. Cl.
CPC .......... *A61N 5/0613* (2013.01); *A61N 5/0625* (2013.01); *B32B 15/04* (2013.01); *A61F 2007/0001* (2013.01); *A61N 2005/066* (2013.01); *A61N 2005/0645* (2013.01)

(58) Field of Classification Search
CPC .................................................... A61N 5/0625
See application file for complete search history.

(56) References Cited

U.S. PATENT DOCUMENTS

2017/0142778 A1*   5/2017   Lee ............................ H05B 3/34

* cited by examiner

*Primary Examiner* — Kaitlyn E Smith
(74) *Attorney, Agent, or Firm* — Chun-Ming Shih; HDLS IPR Services (57) ABSTRACT

A far infrared film structure and a method of manufacturing the same are provided in this disclosure. The far infrared film structure includes a substrate, an oxide thin film, and an electrothermal film. The substrate has a metallic foil sheet and a plastic film overlappingly combined with each other. The oxide thin film is combined onto the metallic foil sheet and consists of an oxide gel formed by mixing an oxide powder and a sol. The electrothermal film is combined onto the plastic film, and the electrothermal film, the oxide thin film, and the substrate together constitute a flexible thin plate. Thus, the far infrared film structure is bendable to conform closely to the contours of a human body and also has a high content of the oxide powder. Therefore, the far infrared film structure is convenient to use and has a good far infrared emission rate.

5 Claims, 6 Drawing Sheets

FAR INFRARED FILM STRUCTURE AND METHOD OF MANUFACTURING THE SAME

TECHNICAL FIELD

The present invention relates to a healthcare device which can generate far infrared and, in particular, to a far infrared film structure and a method of manufacturing the same.

BACKGROUND

Far infrared (FIR) is light having wavelengths between 8,000 and 14,000 nm. FIR can produce a resonance effect on the molecules of a human body, thereby improving blood circulation, metabolism and immunity and balancing the PH (power of hydrogen) value in the body. Therefore, in the market, there's been a trend for healthcare devices to incorporate the use of the FIR.

Concerning a heater in the healthcare device, the heater mainly includes a substrate and an electrothermal film combined on the substrate, thereby achieving a warm compress effect. In order to make the heater work in combination with a far infrared function, the substrate is normally a hard board made from minerals or ceramic materials capable of emitting far infrared, or is a soft board added with mineral powders or ceramic powders capable of emitting far infrared. Alternatively, mineral powders or ceramic powders capable of emitting far infrared are added into fibers to fabricate a variety of textile products.

However, these heaters have the following disadvantages. First, when the substrate is a hard board made from minerals or ceramic materials capable of emitting far infrared, the hard board cannot be bent to conform to the contours of a human body, thereby causing inconvenience in use. Second, when the substrate is a soft board added with mineral powders or ceramic powders capable of emitting far infrared, the soft board has a low content of the mineral powders or the ceramic powders in order to keep the soft board sufficiently soft and flexible, or the mineral powders or the ceramic powders have to be enclosed or glued to be fixed, thereby reducing the far infrared emission efficiency. Third, in adding mineral powders or ceramic powders capable of emitting far infrared into fibers, a stretch rate of the fiber should be no more than 5%, and the fiber also absorbs (blocks) far infrared. Consequently, the finished textile products have inferior far infrared emission efficiency, and the far infrared material mixed/added in the fabric is easily washed away after repetitive washing.

Accordingly, the inventor made various studies to overcome the above-mentioned problems, on the basis of which the present invention is accomplished.

SUMMARY

It is an object of the present invention to provide a far infrared film structure and a method of manufacturing the same, wherein the far infrared film structure is bendable to conform to the contours of a human body and includes a high content of oxide powders, so that the far infrared film structure has convenience of use and a high far infrared emission rate.

Accordingly, the present invention provides a far infrared film structure, comprising: a substrate including a metallic foil sheet and a plastic film overlappingly combined with each other; an oxide thin film combined onto the metallic foil sheet, the oxide thin film consisting of an oxide gel formed by mixing an oxide powder and a sol; an electrothermal film combined onto the plastic film, the electrothermal film, the oxide thin film, and the substrate together constituting a flexible thin plate, the electrothermal film including a flexible electrothermal sheet and at least two electrodes, the flexible electrothermal sheet being constituted by two thin film insulating layers covered by a conductive nano-carbon powder layer, the two electrodes being spaced apart from each other and buried in the flexible electrothermal sheet, the two electrodes being electrically connected to the flexible electrothermal sheet; and a blocking layer covering a surface of the electrothermal film away from the oxide thin film, the blocking layer consisting of at least one of a heat insulating material and an insulating material.

Accordingly, the present invention provides a method of manufacturing a far infrared film structure, comprising the following steps: a) providing an oxide powder and a sol, the oxide powder being added to the sol and mixed with the sol to form an oxide gel; b) providing a substrate, the substrate including a metallic foil sheet and a plastic film overlappingly combined with each other by thermal compression, coating the metallic foil sheet with the oxide gel and performing a processing step to form an oxide thin film; c) providing an electrothermal film, the electrothermal film being combined onto the plastic film to form a flexible thin plate, the electrothermal film including a flexible electrothermal sheet and at least two electrodes, the flexible electrothermal sheet being constituted by two thin film insulating layers coated with a conductive nano-carbon powder layer, the two electrodes being spaced apart from each other and buried in the flexible electrothermal sheet, the two electrodes being electrically connected to the flexible electrothermal sheet; and d) providing a blocking layer, the electrothermal film including a surface away from the oxide thin film, the blocking layer covering the surface and consisting of at least one of a heat insulating material and an insulating material.

The present invention also has the following features. First, the oxide thin film consists of an oxide gel formed by mixing an oxide powder and a sol, so that the oxide thin film has sufficient softness and flexibility and also includes a high content of the powder capable of emitting far infrared. The substrate includes a metallic foil sheet and a plastic film overlappingly combined with each other, wherein the metallic foil sheet of the substrate can reflect the far infrared leaving from the human body to the human body and quickly conducts the heat generated from the electrothermal sheet to the far infrared film, and the plastic film can enhance flexibility to thereby prevent the oxide thin film coated on the substrate from generating crimps or having fractures. Therefore, the far infrared film structure has convenience in use and a great far infrared emission rate and a healthcare function.

Second, the far infrared film structure of the present invention further includes the electrothermal film and the blocking layer. The oxide thin film is coated onto the substrate which is then combined with a face side of the electrothermal film. The blocking layer covers a back side of the electrothermal film. The blocking layer consists of at least one of a heat insulating material and an insulating material, so that the far infrared film structure provides safety in use and functions of heat concentration, energy saving and heat insulation.

BRIEF DESCRIPTION OF THE DRAWINGS

The disclosure will become more fully understood from the detailed description, and the drawings given herein below is for illustration only, and thus does not limit the disclosure, wherein.

DETAILED DESCRIPTION

Detailed descriptions and technical contents of the present invention are illustrated below in conjunction with the accompany drawings. However, it is to be understood that the descriptions and the accompany drawings disclosed herein are merely illustrative and exemplary and not intended to limit the scope of the present invention.

Please referring to FIG. 1 to FIG. 7, the present invention provides a far infrared film structure and a method of manufacturing the same, the far infrared film structure 10 comprises a substrate 1, an oxide thin film 2, an electrothermal film 3, and a blocking layer 4.

Figure 1:
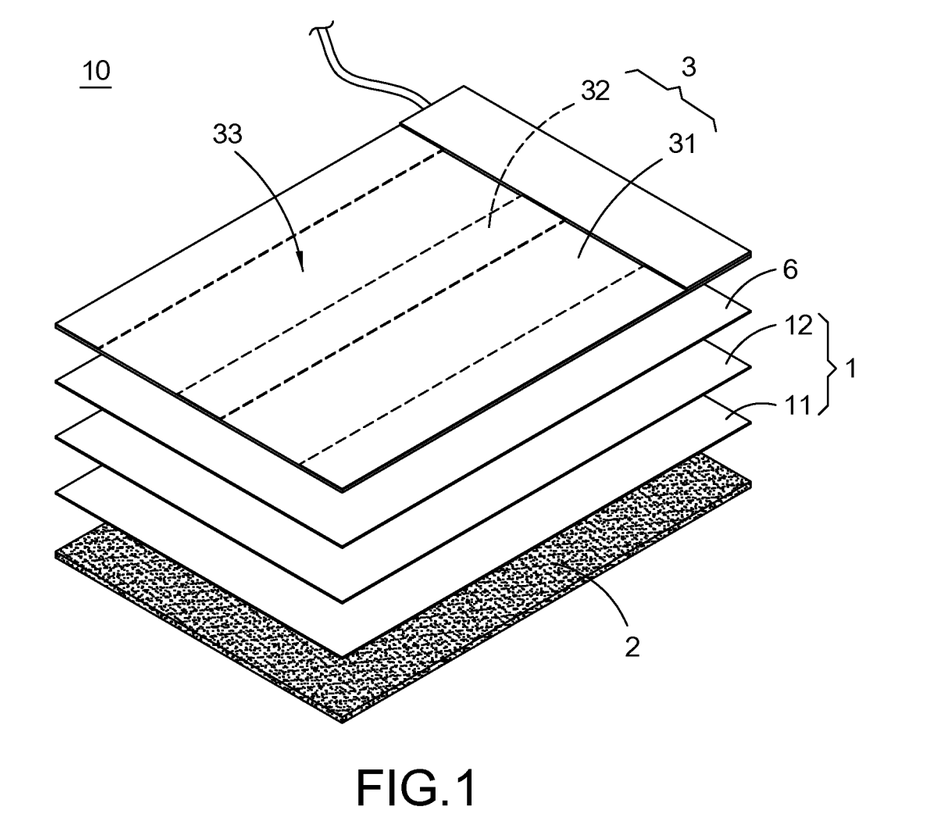
FIG. 1 is a perspective exploded view of a far infrared film structure according to the present invention.
Figure 2:
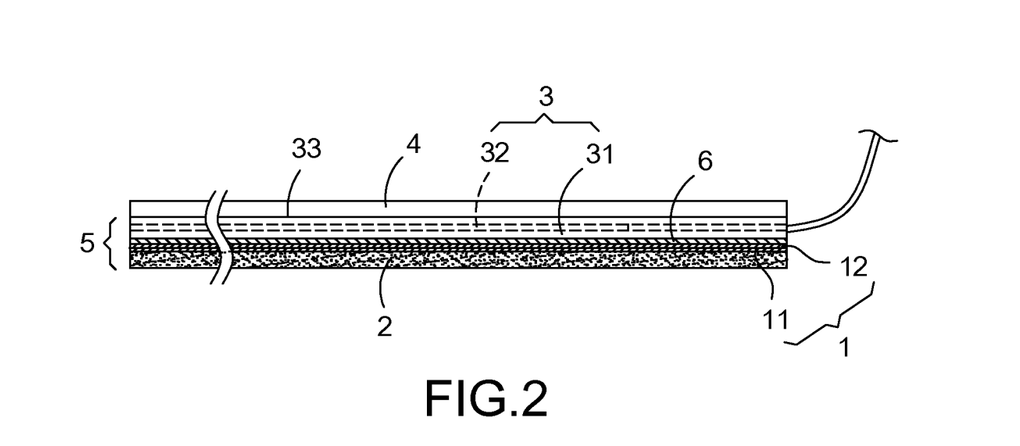
FIG. 2 is an assembly view of the far infrared film structure according to the present invention.

As shown in FIGS. 1 and 2, the substrate 1 has a metallic foil sheet 11 and a plastic film 12 overlappingly combined with each other. The metallic foil sheet 11 can be an aluminum foil sheet or a copper foil sheet. The plastic film 12 can be made of a plastic material such as flexible PET, PE, and PVC.

Referring to FIGS. 1 and 2, the oxide thin film 2 is combined onto the metallic foil sheet 11. The oxide thin film 2 consists of an oxide gel 7 formed by mixing an oxide powder and a sol. The oxide powder can be a mineral powder capable of emitting far infrared, i.e. the oxide powder is selected from a group consisting of iron oxide, manganese oxide, chromium oxide, cobalt oxide, magnesium oxide, titanium oxide, and mixtures thereof above—for example, selected from a group consisting of $SiO_2$, $Al_2O_3$, $Na_2O$, $K_2O$, MgO, CaO, $TiO_2$, $Fe_2O_3$, CoO, $Cr_2O_3$, $MnO_2$, and mixtures thereof; and the sol is silica gel or sodium silicate. Furthermore, the weight percentage of the oxide powder in the oxide thin film 2 is in the range of 50 to 70%. The weight percentage of the sol in the oxide thin film 2 is in the range of 30 to 50%. Regardless of the percentage change between the oxide powder and the sol, it does not affect the flexibility and the functions of the oxide thin film 2 derived from mixing the oxide powder and the sol.

As shown in FIGS. 1 and 2, the electrothermal film 3 is combined onto the plastic film 12. The electrothermal film 3, the oxide thin film 2, and the substrate 1 together constitute a flexible thin plate 5. The electrothermal film 3 includes a flexible electrothermal sheet 31 and at least two electrodes 32. The two electrodes 32 are spaced apart from each other and are electrically connected to the flexible electrothermal sheet 31. The electrothermal film 3 has a surface 33 away from the oxide thin film 2.

The flexible electrothermal sheet 31 is constituted by two thin film insulating layers coated with a conductive nano-carbon powder layer. Since the conductive nano-carbon powder layer is uniform and continuous, it is a flat and continuous type heater. As a result, the far infrared film structure 10 has a uniform electrothermal heating effect.

As shown in FIG. 2, the blocking layer 4 covers a surface 33 of the electrothermal film 3. The blocking layer 4 consists of at least one of a heat insulating material and an insulating material, wherein the insulating material can prevent current leakage from the electrode 32 and the heat insulating material achieves heat concentration and heat insulation.

Referring to FIGS. 1 and 2, the far infrared film structure 10 of the present invention further includes an adhesive layer 6, the adhesive layer 6 is sandwiched between the plastic film 12 and the flexible electrothermal sheet 31, so that the flexible electrothermal sheet 31 is firmly attached to the plastic film 12, and the substrate 1 is thereby firmly attached to the flexible electrothermal sheet 31.

As shown in FIG. 2, in the far infrared film structure 10 of the present invention, the substrate 1 includes a metallic foil sheet 11 and a plastic film 12 overlappingly combined with each other. An oxide thin film 2 is combined onto the metallic foil sheet 11, and the oxide thin film 2 consists of an oxide gel 7 formed by mixing an oxide powder and a sol. An electrothermal film 3 is combined onto the plastic film 12. The electrothermal film 3, the oxide thin film 2, and the substrate 1 together constitute a flexible thin plate 5. The electrothermal film 3 includes a flexible electrothermal sheet 31 and electrodes 32, the flexible electrothermal sheet 31 is coated with a conductive nano-carbon powder layer, the two electrodes 32 are spaced apart from each other and buried in the flexible electrothermal sheet 31, and the electrodes 32 are electrically connected to the flexible electrothermal sheet 31. The block layer 4 covers a surface 33 of the electrothermal film 3 away from the oxide thin film 2, and the blocking layer 4 consists of a heat insulating material or an insulating material. Therefore, the far infrared film structure 10 is bendable to conform the contours of a human body and can include a high content of the oxide powder, so that the far infrared film structure 10 is convenient in use and has a good far infrared emission rate.

Figure 3:
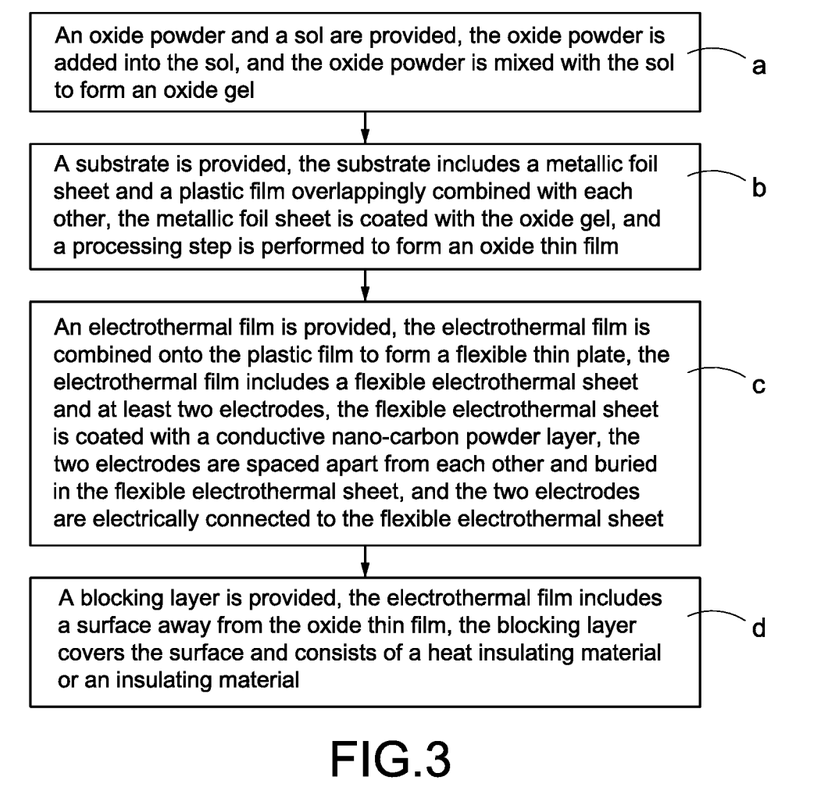
FIG. 3 is a process step flowchart showing a method of manufacturing a far infrared film structure according to the present invention.

Please refer to FIG. 3 which shows steps in a method for manufacturing a far infrared film structure 10. First, in step a of FIG. 3 and FIG. 4, an oxide powder and a sol are provided, the oxide powder is added into the sol and mixed with the sol to form an oxide gel 7.

Figure 4:
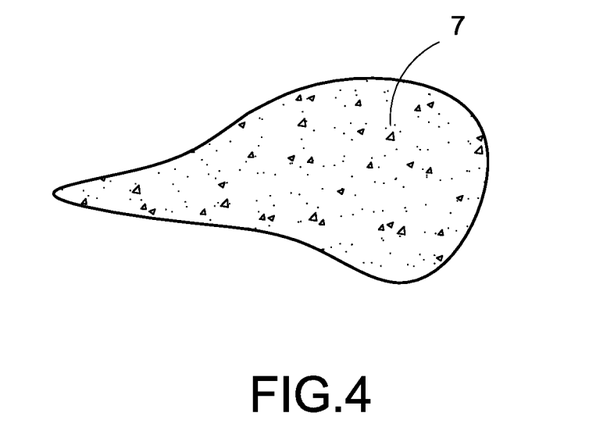
FIG. 4 is a schematic view of the present invention, illustrating that an oxide powder and a sol are mixed to form an oxide gel.
Figure 5:
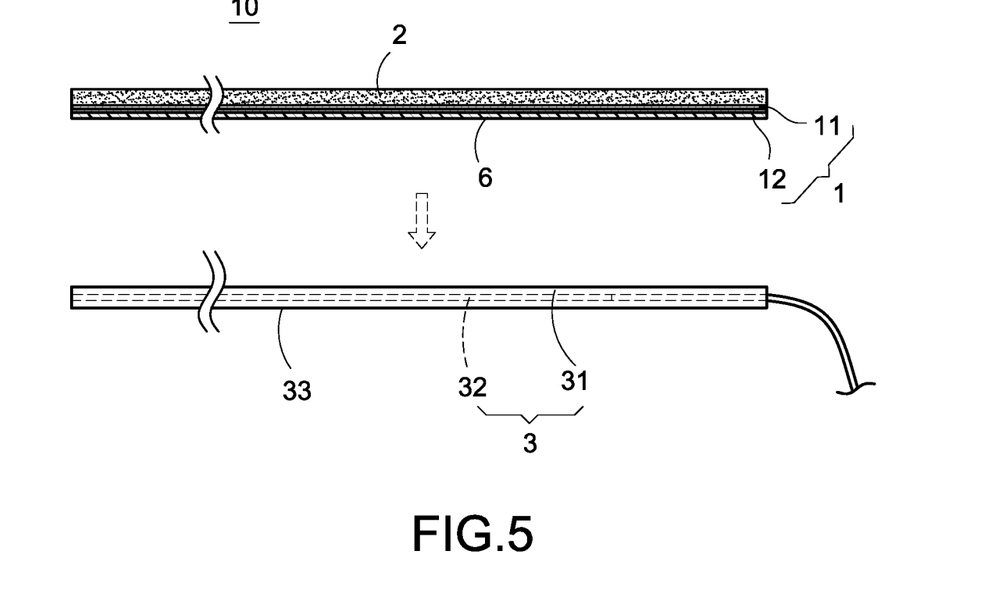
FIG. 5 is a schematic view of the present invention, illustrating that an oxide thin film is to be combined onto an electrothermal film.

Furthermore, as in step b of FIG. 3, and as shown in FIGS. 4 and 5, the substrate 1 is provided, the substrate 1 includes the metallic foil sheet 11 and the plastic film 12 overlappingly combined with each other, the metallic foil sheet 11 is coated with the oxide gel 7, and a processing step is performed to form the oxide thin film 2. This processing step is performing a thermal treatment or air drying on the oxide gel 7 coated on the metallic foil sheet 11 to cure the oxide gel 7 into the oxide thin film 2. The far infrared generated by the oxide thin film 2 is emitted randomly, but the metallic foil sheet 11 reflects the far infrared leaving from a human body to the human body and quickly conducts the heat generated from flexible electrothermal sheet 31 to the oxide thin film 2.

At last, in step c of FIG. 3 and FIG. 5, the electrothermal film 3 and an adhesive layer 6 are provided, the adhesive layer 6 is attached to the plastic film 12, the electrothermal film 3 is then attached to the adhesive layer 6, so the electrothermal film 3 is combined onto the plastic film 12 to together form a flexible thin plate 5.

Figure 6:
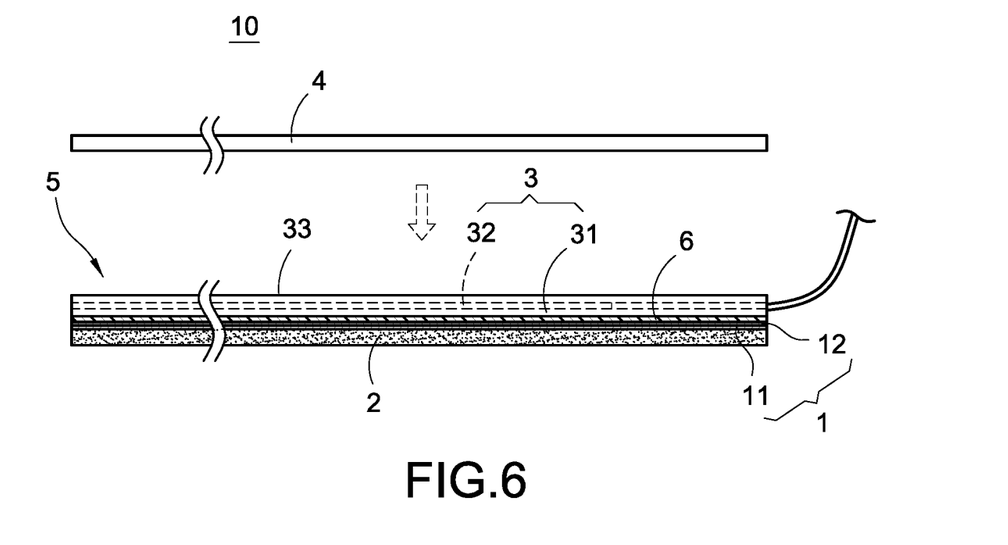
FIG. 6 is a perspective exploded view of the present invention, illustrating that a blocking layer is to cover the electrothermal film.

Moreover, in step d of FIG. 3 and FIG. 6, the blocking layer 4 is provided, the electrothermal film 3 includes a surface 33 away from the oxide thin film 2, and the blocking layer 4 covers the surface 33.

Figure 7:
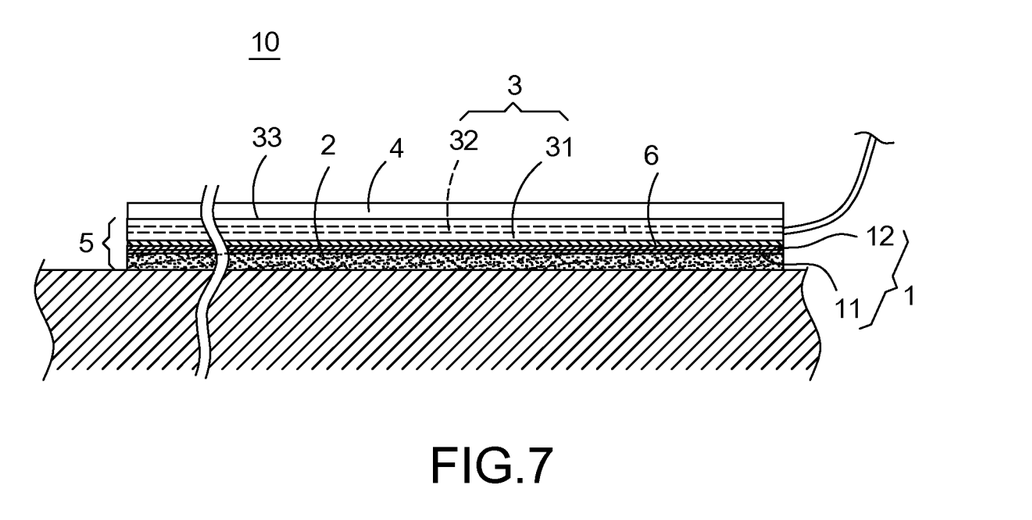
FIG. 7 is a schematic view of the present invention, illustrating the far infrared film structure in use.

Referring to FIG. 7 which illustrates the far infrared film structure 10 in use, the oxide thin film 2 consists of an oxide gel formed by mixing an oxide powder and a sol, so that the oxide thin film 2 has sufficient softness and flexibility and also includes a high content of the powder capable of emitting far infrared. The electrothermal film 3 and the substrate 1 together constitute the flexible thin plate 5, and the blocking layer 4 covers the surface 33 of the electrothermal film 3 to make the far infrared film structure 10 become a layered film structure with different materials superposed in layers (i.e. the electrothermal film 3, the oxide thin film 2, and the blocking layer 4 are superposed in layers), and the layered film structure is capable of emitting far infrared. Since the far infrared film structure 10 is a layered film structure, the far infrared film structure 10 can closely contact the skin, fabrics, or other flexible material, and the oxide thin film 2 alone can also closely contact the skin, fabrics or other flexible materials, so that the far infrared film structure 10 can be bendable as desired to make the oxide thin film 2 conform to the contours of a human body. In addition, the electrothermal film 3 continually generates heat to provide a warm therapy effect. Accordingly, the far infrared film structure 10 has convenience of use and a great far infrared emission rate and a healthcare function.

Moreover, the substrate 1 includes a metallic foil sheet 11 and a plastic film 12 overlappingly combined with each other, wherein the metallic foil sheet 11 of the substrate 1 can reflect the far infrared leaving from the human body to the human body and quickly conducts the heat generated from the flexible electrothermal sheet 31 to the oxide thin film 2, the plastic film 12 closely contacts and protects the metallic foil sheet 11, and the plastic film 12 can enhance flexibility of a finished product to thereby prevent the oxide thin film 2 coated on the substrate 1 from generating crimps or having fractures. Thus, the metallic foil sheet 11 is prevented from having fractures or being broken when the far infrared film structure 10 is bent.

Furthermore, the oxide thin film 2 can be combined onto all kinds of soft or hard objects, so as to generate far infrared from the surface of the object by using the heat of the object and the oxide thin film, and thereby the far infrared film structure 10 can be used extensively and provide a good healthcare function.

Moreover, the far infrared film structure 10 of the present invention further includes the blocking layer 4. The blocking layer 4 covers the electrothermal film 3. The blocking layer 4 consists of a heat insulating material and an insulating material, thereby preventing current leakage from the electrodes 32 and achieve heat concentration and heat insulation, so that the far infrared film structure 10 provides safety in use and functions of heat concentration, energy saving and heat insulation.

In addition, the far infrared film structure 10 further includes a controller (not illustrated), the controller is electrically connected to the electrothermal film 3, and the controller is configured to maintain the electrothermal film 3 at a constant temperature or to provide a timer function.

Figure 8:
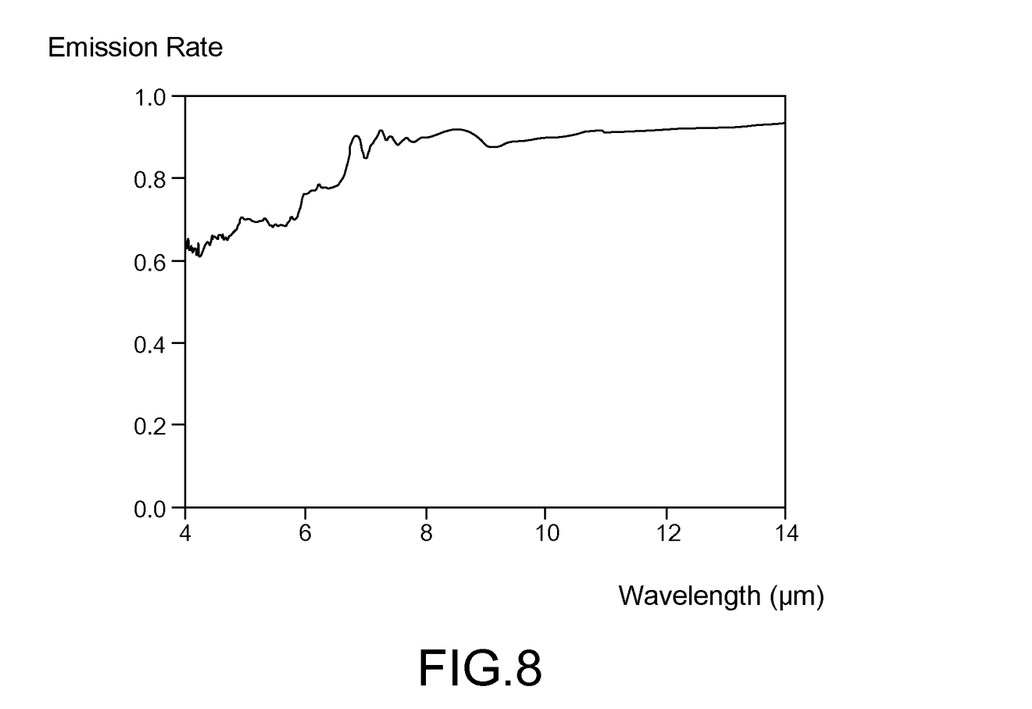
FIG. 8 is a graph showing a far infrared emission rate of the oxide thin film according to the present invention.
Figure 9:
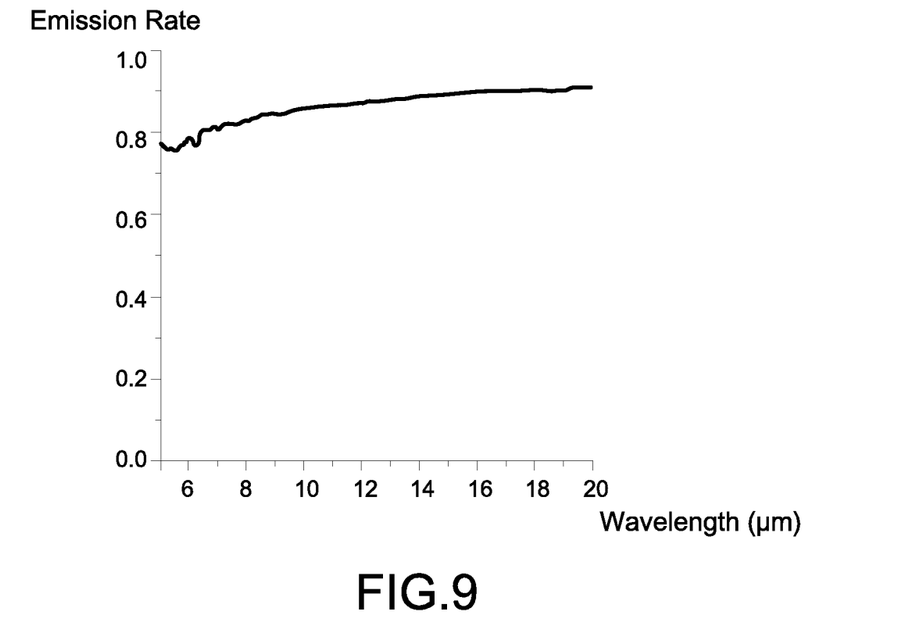
FIG. 9 is another graph showing the far infrared emission rate of the oxide thin film according to the present invention.
Figure 10:
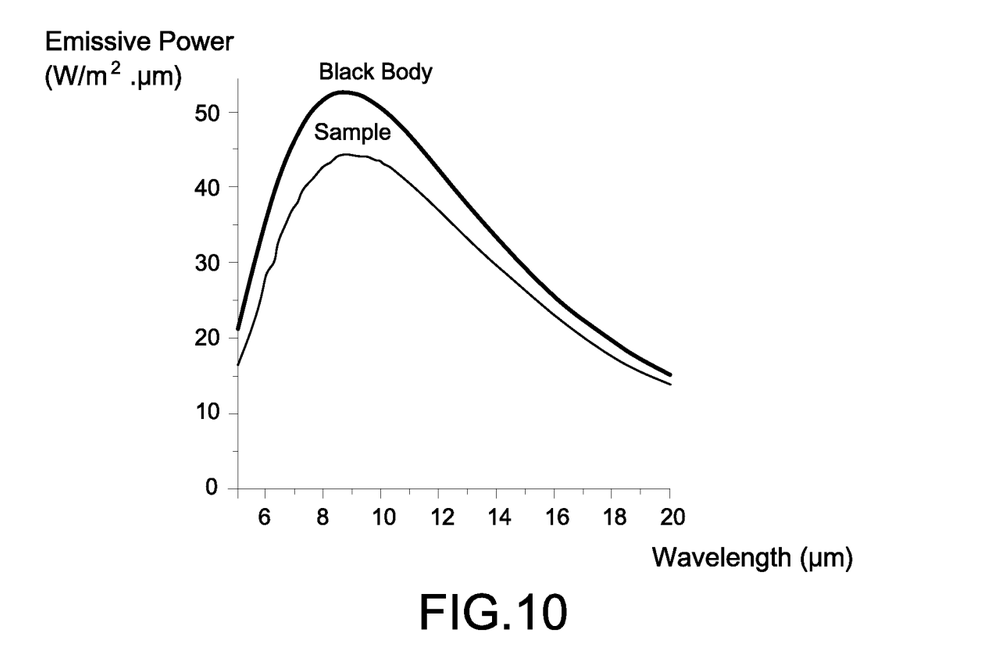
FIG. 10 is a graph showing a far infrared emissive power of the oxide thin film according to the present invention.
Figure 11:
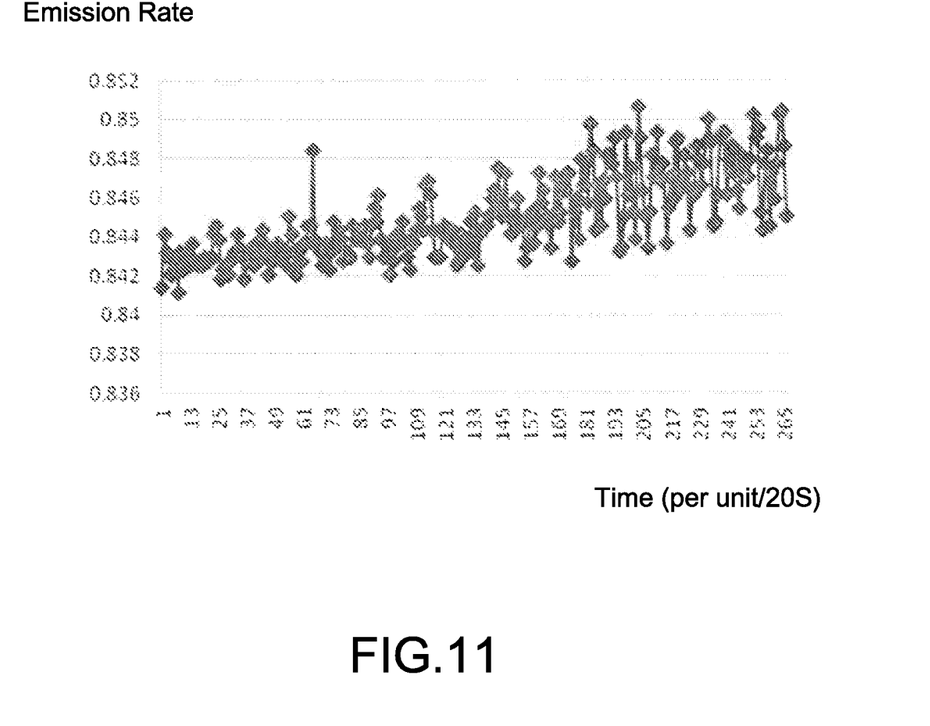
FIG. 11 is another graph showing the far infrared emission rate of the oxide thin film according to the present invention.

Please refer to FIGS. 8 to 11 which are graphs showing a far infrared emission rate and a far infrared emissive power of the oxide thin film 2 according to the present invention. FIG. 8 is a graph of the far infrared emission rate measured by Industrial Technology Research Institute of Taiwan, the environmental condition being in a laboratory at a temperature of 25° C. and a relative humidity of 60%. FIG. 9 is another graph showing the far infrared emission rate measured by Korea Research Institute, the environmental condition being in a laboratory at a temperature of 60° C. FIG. 10 is a graph showing a far infrared emissive power measured by Korea Research Institute, the environmental condition being in a laboratory at a temperature of 60° C., wherein "Sample" is the data of the oxide thin film 2 of the present invention, and "Black Body" is the maximum theoretical value in nature. FIG. 11 is a graph showing the far infrared emission rate detected by National Taiwan Craft Research and Development Institute, the environmental condition being in a laboratory at a temperature of 34° C. and a relative humidity of 45%. According to the foregoing graphs showing the far infrared emission rate and the far infrared emissive power of the oxide thin film 2, the oxide thin film 2 of the present invention can emit far infrared with high energy and has a great far infrared emission ability.

It is to be understood that the above descriptions are merely the preferable embodiments of the present invention and are not intended to limit the scope of the present invention. Equivalent changes and modifications made in the spirit of the present invention are regarded as falling within the scope of the present invention.

What is claimed is:

1. A far infrared film structure, comprising:
a substrate including a metallic foil sheet and a plastic film overlappingly combined with each other;
an oxide film combined onto the metallic foil sheet, the oxide film consisting of an oxide gel formed by mixing an oxide powder and a sol;
an electrothermal film combined onto the plastic film, the electrothermal film, the oxide film, and the substrate together constituting a flexible plate, the electrothermal film including a flexible electrothermal sheet and at least two electrodes, the flexible electrothermal sheet being constituted by two insulating layers covered by a conductive nano-carbon powder layer, the two electrodes being spaced apart from each other and buried in the flexible electrothermal sheet, the two electrodes being electrically connected to the flexible electrothermal sheet; and
a blocking layer covering a surface of the electrothermal film away from the oxide film, the blocking layer consisting of at least one of a heat insulating material and an electrical insulating material.

2. The far infrared film structure of claim 1, wherein the oxide powder is selected from a group consisting of iron oxide, manganese oxide, chromium oxide, cobalt oxide, magnesium oxide, titanium oxide, and mixtures thereof above, and the sol is silica gel or sodium silicate.

3. The far infrared film structure of claim 2, wherein the weight percentage of the oxide powder in the oxide film is in the range of 50 to 70%.

4. The far infrared film structure of claim 2, wherein the weight percentage of the sol in the oxide film is in the range of 30 to 50%.

5. The far infrared film structure of claim 1, further comprising an adhesive layer, the adhesive layer being sandwiched between the plastic film and the electrothermal film.

* * * * *